United States Patent
Meinke et al.

(10) Patent No.: US 12,121,745 B2
(45) Date of Patent: Oct. 22, 2024

(54) DEVICE AND METHOD FOR UV ANTISEPSIS

(71) Applicants: UNIVERSITÄTSMEDIZIN GREIFSWALD, Greifswald (DE); CHARITÉ—UNIVERSITÄTSMEDIZIN BERLIN, Berlin (DE); TECHNISCHE UNIVERSITÄT BERLIN, Berlin (DE); FERDINAND-BRAUN-INSTITUT GGMBH, LEIBNIZ-INSTITUT FÜR HÖCHSTFREQUENZTECHNIK, Berlin (DE)

(72) Inventors: Martina Meinke, Berlin (DE); Jürgen Lademann, Fürstenwalde (DE); Axel Kramer, Greifswald (DE); Michael Kneissl, Berlin (DE); Tim Wernicke, Berlin (DE); Ulrike Winterwerber, Berlin (DE); Sven Einfeldt, Berlin (DE)

(73) Assignees: UNIVERSITÄTSMEDIZIN GREIFSWALD, Greifswald (DE); ; CHARITÉ —UNIVERSITÄTS-MEDIZIN BERLIN, Berlin (DE); TECHNISCHE UNIVERSITÄT BERLIN, Berlin (DE); FERDINAND-BRAUN-INSTITUT GGMBH, LEIBNIZ-INSTITUT FÜR HÖCHSTFREQUENZTECHNIK, Berlin (DE)

( * ) Notice: Subject to any disclaimer, the term of this patent is extended or adjusted under 35 U.S.C. 154(b) by 318 days.

(21) Appl. No.: 17/640,608

(22) PCT Filed: Aug. 12, 2020

(86) PCT No.: PCT/EP2020/072631
§ 371 (c)(1),
(2) Date: Mar. 4, 2022

(87) PCT Pub. No.: WO2021/043554
PCT Pub. Date: Mar. 11, 2021

(65) Prior Publication Data
US 2022/0339467 A1 Oct. 27, 2022

(30) Foreign Application Priority Data

Sep. 6, 2019 (DE) .................... 10 2019 124 017.4

(51) Int. Cl.
*A61N 5/06* (2006.01)

(52) U.S. Cl.
CPC ...... *A61N 5/0624* (2013.01); *A61N 2005/063* (2013.01); *A61N 2005/0652* (2013.01);
(Continued)

(58) Field of Classification Search
CPC ............ A61N 5/0624; A61N 2005/063; A61N 2005/0652; A61N 2005/0661;
(Continued)

(56) References Cited

U.S. PATENT DOCUMENTS

2006/0167531 A1* 7/2006 Gertner ................ A61N 5/0603
607/86
2011/0317397 A1* 12/2011 Trottier ................ H01L 33/502
445/44

(Continued)

FOREIGN PATENT DOCUMENTS

CN 109742210 A * 5/2019
EP 3195900 A1 7/2017

(Continued)

OTHER PUBLICATIONS

International Search Report mailed Oct. 13, 2020, in connection with PCT International Application No. PCT/EP2020/072631.
(Continued)

*Primary Examiner* — Jonathan T Kuo
(74) *Attorney, Agent, or Firm* — Norris McLaughlin, P.A.

(57) ABSTRACT

The invention relates to a device and a method for UV antisepsis, in particular for intracorporeal in vivo UV antisepsis on the human and animal body in the event of colonization with multiresistant pathogens (MRPs) such as methicillin-resistant *Staphylococcus aureus* (MRSA) and *Staphylococcus epidermidis* (MRSE). The device comprises a light emitting diode chip, LED chip, configured to emit radiation in the UVC spectral range, wherein the LED chip forms a light emitting diode, LED, with a package; a spectral filter element set up to limit the radiation emitted by the LED chip substantially to wavelengths below 235 nm; and an (Continued)

optical element for directional emission of the radiation emitted by the LED.

13 Claims, 5 Drawing Sheets

(52) U.S. Cl.
CPC ............. *A61N 2005/0661* (2013.01); *A61N 2005/0666* (2013.01)

(58) Field of Classification Search
CPC .... A61N 2005/0666; A61N 2005/0667; A61N 2005/0665; A61N 5/06–2005/073
See application file for complete search history.

(56) References Cited

U.S. PATENT DOCUMENTS

| | | | |
|---|---|---|---|
| 2013/0270445 A1 | 10/2013 | Gaska et al. | |
| 2016/0303394 A1* | 10/2016 | Hayashi | .................... A61L 2/10 |
| 2018/0043043 A1 | 2/2018 | Spector et al. | |
| 2022/0339467 A1 | 10/2022 | Meinke et al. | |

FOREIGN PATENT DOCUMENTS

| | | |
|---|---|---|
| EP | 4 025 297 A1 | 7/2022 |
| WO | 2015/006309 A1 | 1/2015 |
| WO | 2019/077817 A1 | 4/2019 |
| WO | 2021/043554 A1 | 3/2021 |

OTHER PUBLICATIONS

English translation of International Search Report mailed Oct. 13, 2020, in connection with PCT International Application No. PCT/EP2020/072631.

Written Opinion issued in connection with PC T International Application No. PCT/EP2020/072631.

Ponniaya et al., "Far-UVC Light Prevents MRSA Infection of Superficial Wounds in vivo", PLOS ONE, No. 13, vol. 2, pp. 1-12, Feb. 2018.

* cited by examiner (Prior Art)

DEVICE AND METHOD FOR UV ANTISEPSIS

This application is the U.S. National Stage of International Application No. PCT/EP2020/072631, filed Aug. 12, 2020, which claims foreign priority benefit under 35 U.S.C. § 119 of German Application No. 10 2019 124 017.4, filed Sep. 6, 2019.

DESCRIPTION

The invention relates to a device and a method for UV antisepsis, in particular for intracorporeal in vivo UV antisepsis on the human and animal body in the event of colonization with multiresistant pathogens (MRPs) such as methicillin-resistant *Staphylococcus aureus* (MRSA) and *Staphylococcus epidermidis* (MRSE).

The pandemic spread of multiresistant pathogens (MRPs) is leading to increased infections worldwide with associated increased mortality, particularly among intensive care patients. Existing decolonization concepts have been insufficiently successful. MRPs decolonization is currently mainly performed by means of antisepsis. However, the success rate is well below 50%. Substantial regions of the body are moreover inaccessible to antisepsis.

UV antisepsis (also denoted UV sterilization or UV disinfection) of surfaces or medical equipment is typically performed with UV mercury vapor lamps or UV LEDs which emit at 254 nm or in the 250 nm to 285 nm wavelength range. The wavelength is selected on the basis of the fact that the effect of UV radiation ("Germicidal Effectiveness") is at its highest in this wavelength range. This is radiation in particular from the UVC range, to which wavelengths of between 100 nm and 280 nm are by definition assigned. In UV antisepsis, the applied radiation causes irreversible damage to the genetic information of bacteria and viruses resulting in the breakdown of their metabolic processes. UVC radiation can also be used on humans (e.g. for antisepsis of pathogens, in particular MRSA and MRSE), but involves the problem that the UVC radiation in these wavelength ranges penetrates deep into the layers of the skin and also results in corresponding damage to healthy human tissue.

Recently published studies have revealed that in particular shortwave radiation with wavelengths of ≤230 nm does not penetrate deeply into the skin, mucosa or wounds due to high absorption in the upper skin layers, i.e. it cannot overcome the skin barrier [B. Ponnaiya et al., Far-UVC light prevents MRSA infection of superficial wounds in vivo, PLOS ONE 2018, 13(2): e0192053)]. One reason for this is the wavelength dependence of the absorption coefficient of skin, which increases significantly for wavelengths of <250 nm [M. Bounnano et al., 207-nm UV Light—A Promising Tool for Safe Low-Cost Reduction of Surgical Site Infections. I: In Vitro Studies., PLOS ONE 2013, 8(10): e76968]. It may be concluded therefrom that, at a depth of 18 μm from the skin's surface, UV radiation at 233 nm is about 100× more strongly attenuated than UV radiation at 254 nm. The relative intensity is here attenuated by a factor of $10^{-4}$ in comparison with the intensity at the surface. The differences in the harmful effect of UV radiation at 222 nm and 254 nm with different doses have already been demonstrated in basal cells with cis-syn cyclobutane-pyrimidine dimer (CPD) on mouse skin [Saadati S., Study of ultraviolet C light penetration and damage in skin, Columbia Univ/Univ Gothenburg, 2016: https://radfys.gu.se/digitalAssets/1616/1616169_study-of-ultraviolet-c-light-penetration-and-damage-in-skin.pdf].

WO 2019/077817 A1 discloses that UV antisepsis with radiation from a wavelength range of 190 nm or above to 230 nm or below is suitable for bringing about an antiseptic action on a target organism to be decolonized without in so doing damaging its animal or human cells. A corresponding device and a method for sterilization, in particular in the event of colonization with *Staphylococcus aureus* (*S. aureus*) are proposed. The disclosed devices are, however, based on gas discharge or excimer lamps and are therefore not suitable for applications in clinical intracorporeal antisepsis due to the complex light guidance required for UV radiation. These devices moreover generate considerable quantities of thermal radiation, which means that direct in vivo use on living skin is likewise only possible to a limited extent.

Apart from this, however, UVC radiation with wavelengths ≤230 nm is in principle suitable for killing pathogens, in particular MRPs, on surfaces even within the body without any risk of side-effects. The radiation dose required to kill MRPs is <100 mJ/cm². In patients with MRSA colonization in the nasal cavity, throat or wounds, decolonization without antiseptics could thus be achieved. In the event of colonization by MRPs, in particular by Gram-negative bacteria and enterococci, in body cavities such as the nasal sinuses, uterus, urinary bladder or intestinal tract, the use of antiseptics is not possible. Antibiotics can only be used therapeutically, but not for decolonization. Local treatment capable of having an in situ microbicidal effect would be desirable in such cases. This does, however, require devices and methods which are also suitable for performing intracorporeal in vivo UV antisepsis on the human and animal body. In particular, the complexity of wave guidance in the UV range and the impossibility of performing uniform and large-area local irradiation also on intracorporeal three-dimensional tissue structures have so far prevented clinical application. A further difficulty is the evolution of heat from previously used radiation sources which entails a minimum distance between the surface of the skin or tissue and thus likewise limits the potential range of applications.

The object of the present invention is to overcome or at least reduce the problems of the prior art and to provide a device and a method in particular for intracorporeal in vivo UV antisepsis on the human and animal body. The essential object of the invention is to provide a device which enables the decolonization of different surfaces and cavities in particular in humans (for example the nasal cavity including nasal sinuses, throat, wounds) without causing any damage to the correspondingly treated tissue (skin, mucous membrane).

The invention relates to a device for UV antisepsis, comprising a light-emitting diode chip, LED chip, configured to emit radiation in the UVC spectral range, wherein the LED chip forms a light-emitting diode, LED, with a package; a spectral filter element, set up to restrict the radiation emitted by the LED chip substantially to wavelengths below 235 nm, more preferably below 230 nm, and still more preferably below 225 nm; and an optical element for directional emission of the radiation emitted by the LED.

The LED chip may preferably be a group III nitride UV LED with an epitaxial multilayer structure applied to a substrate of sapphire ($Al_2O_3$) or AlN, which emits substantially in a wavelength range of 210 nm to 240 nm. A UV LED is usually constructed therefrom using the flip-chip method, wherein the contact layers of the LED chip are contacted by means of a submount provided with metal electrodes. The generated radiation is in this case emitted through the substrate, i.e. through the bottom of the LED chip. The submount with the LED chip is conventionally protected from environmental influences by encapsulation. This encapsulation forms the package, wherein the encapsulated components are then usually collectively referred to as LEDs. For directional emission of the radiation emitted by the LED, the package may include a transparent optical element, such as an exit window, exit lens, or beam-shaping element. Since the choice of transparent materials is severely limited in the UV range, high-purity silica glass is conventionally used for the optical element. In particular, the optical element may form the cap of the package encapsulation. The term emission refers to direct emission onto the surfaces to be decolonized, without any further optical elements being involved thereafter. The term directional means, in particular, that emission can be targeted onto a surface to be decolonized.

A device according to the invention for UV antisepsis can also comprise a plurality of LEDs according to the invention, which form a common LED module. Preferably, such an LED module has a housing for accommodating the LEDs, which may in turn be arranged on a common circuit carrier (PCB—printed circuit board). Like the package, the housing can have an optical element for directional emission of the radiation emitted by the LEDs. In particular, this may be a cover made of silica glass. The LED module can include a plurality of LED chips with or without an individual package. In a broader sense, arranging multiple LED chips or LEDs within a common housing can also be considered packaging.

Possible applications may be found especially in the clinical field for patients colonized with MRSA or other MRPs. By decolonizing the nasal cavity, throat, wounds and other body cavities with UV LED irradiation, it should be possible to prevent infections in patients and the further spread of MRPs. In particular, the present invention describes the use of particularly short-wave UVC radiation from LEDs for direct irradiation of patients' skin, mucous membranes, or wounds to kill microorganisms without causing significant damage. The mode of action of UV antisepsis resides in damaging the DNA of the microorganisms. Tolerability of the method is ensured by the small wavelength of the LED light, as a result of which the light is virtually completely absorbed in the stratum corneum of the skin and does not damage the underlying living epidermis.

The devices according to the invention, also referred to as DUV (deep ultraviolet) LED emitter modules, are particularly well suited to intracorporeal in vivo antisepsis. Appropriate LEDs have sufficiently high power densities per unit area and a broad UV spectrum, these being advantageous for high irradiation efficiency with potentially harmless evolution of heat. However, the challenge in designing a DUV LED emitter module is to achieve a sufficiently high power density per unit area in the wavelength range <235 nm, but at the same time avoid the emission of longer wavelength UVC and UVB radiation components, i.e. radiation with wavelengths >235 nm, as these can penetrate into deeper skin layers and damage human tissue. To enable efficient antisepsis with short irradiation times, the irradiated power should be selected to be as high as possible. However, if the power density is too high, tissue damage can also occur, particularly due to thermal effects. It must be noted in this respect that the self-heating of the LEDs or the LED module, which increases with increasing operating current (and thus higher power density), must be limited in order to avoid tissue damage due to thermal effects. An optimum point must therefore be found between the selected cut-off wavelength (to avoid radiation-induced tissue damage) and a radiation dose required for adequate antisepsis.

Investigations with filtered Kr—Cl excimer lamps (emission at 222 nm) show that at this wavelength and an irradiation dose of 50 mJ/cm$^2$ no or hardly any damage occurs in the tissue and nevertheless decolonization of the surface is observed. Initial investigations with a frequency-doubled Ar laser (laser emission at 229 nm) on excised skin also found no or hardly any damage to the tissue up to an irradiation dose of 300 mJ/cm$^2$. Whereas the use of excimer lamps is limited by their significant emission of heat and associated skin heating, UV LEDs are inherently cold emitters in which the waste heat can be effectively dissipated to the side remote from the skin and controlled by limiting the electrical power. In this respect, the emission of heat of a UV LED is not critical. Furthermore, due to the tubular design of excimer lamps, UV application is only possible to a limited extent in the case of skin areas that are difficult to access or arbitrary in size, while flexible large-area emitter geometries can also be achieved using an arrangement of multiple UV LEDs.

Since the emission spectra of UV LEDs have a finite half-width (the FWHM is typically 8-14 nm) and in some cases parasitic luminescence ("defect luminescence") additionally also occurs in the longer-wavelength UV range, care must be taken in the DUV LED module for UV antisepsis to ensure that these spectral components have the lowest possible intensities or are eliminated completely. For this purpose, the device has a spectral filter element. One way to implement this is to integrate an optical short-pass filter (or alternatively a band-pass filter with a corresponding lower band edge when used as a short-pass filter) into the package or directly into or onto the LED chip. Such an optical short-pass filter can be produced, for example, by means of UV-transparent dielectric layer stacks. For example, in a group III nitride-based UV LED, such a short-pass filter could be composed of 10 AlO$_x$/SiO$_2$ mirror pairs. Such an optical DBR (distributed Bragg reflector) can be integrated directly into the LED chip during epitaxy. However, the DBR can also be applied to the LED chip, for instance by depositing the mirror pairs onto the rear of a polished sapphire substrate of the LED chip. Another possibility is to integrate the mirror pairs into the UV LED package, e.g. as part of a silica glass capping of the package. When designing a spectral filter element matching the spectral distribution of the emission of an LED chip, the sideband reflectivities can also be adjusted (e.g. chirped DBR mirror) or the width of the stopband (e.g. other dielectrics such as HfO$_2$) can be influenced.

For example, the reflectivity of an AlO$_x$/SiO$_2$ DBR can be set such that it is minimal at 233 nm and increases very rapidly for longer UV wavelengths (i.e. these wavelengths are filtered out). Due to a practical limit on the number of possible filter layers, the short pass will generally be a bandstop filter with a corresponding band edge at the desired stopband wavelength. However, with 10 AlO$_x$/SiO$_2$ mirror pairs it is already possible to achieve stopband widths of about 60 nm, such that such a filter element can be made substantially transparent to wavelengths of below 233 nm and reflective (i.e. blocking) for wavelengths between 233 nm and about 293 nm. This is sufficient to prevent skin damage, since the typical emission spectrum of a DUV LED with a maximum intensity at 233 nm is substantially limited to wavelengths of between 220 nm and 260 nm.

The radiation dose required for $\log_{10}$ decolonization is likewise wavelength-dependent (and also different for different microorganisms). For UV antisepsis for *E. coli*, the maximum of the action spectrum is at 265 nm to 270 nm and decreases towards shorter wavelengths. To achieve a $\log_{10}$ reduction for an *E. coli* bacterium, an irradiation dose of 7 mJ/cm² is required at a wavelength of 265 nm, while an irradiation dose of as high as 20 mJ/cm² is required at 230 nm. The bacterium *S. aureus* has a slightly lower deactivation constant k compared to *E. coli* (*E. coli*: k=0.10575 m²/J, *S. aureus*: k=0.07132 m²/J, both for surface irradiation with an irradiation wavelength of 254 nm), such that for a $\log_{10}$ reduction at 230 nm a slightly higher irradiation dose of 30 mJ/cm² must be expected [W. Kowalski, "Ultraviolet Germicidal Irradiation Handbook", Springer 2009].

The maximum power of UV LEDs with a maximum intensity at a wavelength of 233 nm is currently about 1.5 mW, wherein this typically decreases to 30% to 50% of the output power over a period of 100 hours and then drops only slightly, i.e. the long-term stable power is currently at a maximum of about 0.5 mW. Even with this relatively low power, however, it is possible to produce a DUV LED module that can be used in a clinical environment. When the power is irradiated onto an area of one square centimeter, the power density per unit area is 0.5 mW/cm². To achieve an irradiation dose of 30 mJ/cm², an irradiation time of at most 60 s, i.e. about one minute, is thus required. This is already a feasible period for clinical UV antisepsis. However, it can be assumed that with the improvement of LED technology, still significantly shorter irradiation times will be possible in the future. An increase in the output power by at least one order of magnitude, e.g. by means of growth of DUV LEDs on bulk AlN, seems realistic here. The necessary irradiation time would then be reduced to less than 6 s and clinical application would thus even be possible during surgery. No method is yet known that can effectively reduce postoperative wound infections in the OR environment (surgical side infection, SSI). Particularly in the case of prolonged operations, intermediate antiseptic treatment is usually not possible. Radiation antisepsis accompanying surgery could be effective in preventing the person undergoing surgery from being colonized with pathogens. If decolonization by MRSA or other MRPs is not possible or has not been successful preoperatively, antisepsis accompanying the operation in the OR environment is of particular importance.

Another way to increase the light output of DUV LEDs is to operate the LED in pulsed mode. By driving with very short electrical pulses (a few 100 ns up to 1 µs), heating effects within the LED chip can be avoided. This allows the LEDs to operate at higher currents or current densities, resulting in high pulse energy. This can be used to increase maximum average power or to enhance deactivation efficiency. Pulsed irradiation can also reduce the necessary irradiation time with current DUV LEDs compared to uninterrupted continuous operation.

One problem with integrating optical filters and UV LEDs is that emission from the LEDs occurs across all solid angles. In the case of a UV LED constructed using the flip-chip method, the UV light is typically emitted into the upper half-space through the UV-transparent substrate (e.g. sapphire) into all solid angles. Since the light rays must pass through different effective layer thicknesses depending on the angle of incidence in the case of a planar layer structure of the spectral filter element, it follows that the cut-off wavelength of the dielectric short-pass filters (or correspondingly used band-pass filters) varies with the angle of incidence of the UV rays. For optimal filtering, therefore, this angle-dependent shift in the cutoff wavelength of the dielectric short-pass filters or band-pass filters should be avoided.

Preferably, the shape of the spectral filter element can be adapted to the emission characteristics of the LEDs. In particular, this can be achieved by applying the individual mirror layers of a spectral filter element (DBR) described above to a hemispherical cap (or cover) made for example of UV-transparent silica glass or silicone. In this case, the effective layer thickness traversed by the radiation is the same for all spatial directions. In the case of an array arrangement of multiple LEDs, a semi-cylindrical cap (cover) can also be used instead. Angular independence can then be brought about at least in axes perpendicular to the orientation of the lines of the array.

Other approaches to angle-independent filters are known from Yi-Jun Jen et al. (Design and Fabrication of a Narrow Bandpass Filter with Low Dependence on Angle of Incidence, Coatings, 8(7):231 (2018)) and L. Lin et al. (Angle-robust resonances in cross-shaped aperture arrays, Applied Physics Letters 97, 061109 (2010)).

In L. Lin et al., a virtually angle-independent bandpass filter is obtained via excitation of localized surface plasmons in cross-shaped holes in 140 nm thick silver films on glass. The cross-shaped holes have a length of around 240 nm and are arranged with a period of 360 nm in 2 dimensions. However, the design is for a filter in the infrared range (bandpass with a wavelength of about 1000 nm). Preferably, such a design is applied to UV wavelengths and used as a spectral filter element for the purposes of this invention. However, the dimension of the cross structures and the period must be designed significantly smaller for this purpose, preferably by a factor of 3 to 5. In addition, instead of silver, other metals with a higher plasma frequency, e.g. aluminum, are preferably used for production. A corresponding spectral filter element can then be applied, for example, to UV-transparent silica glass or another UV-transparent dielectric material.

Yi-Jun Jen et al., also disclose a virtually angle-independent bandpass filter. The Fabry-Perot filter concept (FP filter concept) is here based on the combination of metal layers and dielectrics as mirror layers. An FP filter consisting of 5 layers with the sequence air/Ag(13 nm)/silicon(90 nm)/Ag (10 nm)/silicon(97 nm)/Ag(20 nm) was deposited on glass. This layer sequence enables a virtually angle-independent bandpass filter in the infrared spectral range at a wavelength of 900 nm. Preferably, this design is also applied to UV wavelengths and used as a spectral filter element for the purposes of this invention. The layer thicknesses must be adapted accordingly, i.e. preferably reduced by a factor of 3 to 5. Preferably, instead of silver, other metal with a higher plasma frequency, e.g. aluminum, is used for production. UV-transparent dielectrics ($Al_2O_3$ or $HfO_2$, $CaF_2$) can then be applied to e.g. UV-transparent silica glass or another UV-transparent dielectric material.

Preferably, at least one monitor diode (photodiode) can be integrated into the light-emitting diode or the device as a detector for monitoring the radiant power irradiated onto the surface to be decolonized. This allows continuous monitoring of the emitted or radiated power and can be used, in particular, to detect a defect in the device or improper use.

The spatial emission characteristics of the LED are preferably determined by way of the width, composition and distortion of the band structure of the LED chip, the external geometry of the LED chip or by reflectors and apertures integrated into the package. Corresponding freedoms in the design of UV LEDs and lamps based thereon make it possible to adjust the spatial radiation characteristic in a defined way. This is especially useful for in vivo irradiation applications. For example, in order to minimize the damaging effect of UVC radiation on the skin, on the one hand the wavelength can be kept as small as possible, and on the other irradiation can proceed under more glancing than perpendicular incidence on the skin. While reducing the wavelength well below 230 nm is problematic due to the associated decrease in radiant power, the angle of incidence can be influenced by radiation geometric freedoms in the design of the LED or a radiator based thereon.

Furthermore, when irradiating surfaces, the spatial uniformity of the radiant power is important to ensure the effectiveness of the method over the irradiated area. When radiating into body openings, on the other hand, emission should be as uniform as possible over the entire solid angle in order to be able to completely illuminate the inner surface of the body opening. To eradicate pathogens on a topologically complex body surface, shallow emission angles are required to irradiate beneath shading structures. It is therefore preferred for the optical element according to the invention to be adapted or adaptable to the respective irradiation situation. For example, it is advantageous for emission to proceed within body cavities in such a way that the body cavity is filled by the optical element in a largely form-fitting manner and for irradiation to proceed via the entire element structure located in the body cavity. By filling in maximally form-fitting manner, a uniform distance can be established between the surface to be irradiated and the optical element.

The spatial emission of UV LEDs and radiators based thereon can be individually adapted in many ways. The spatial emission of the LED chip also depends, inter alia, on the band structure of the active zone. The width, composition and distortion thereof can influence the band structure (and thus also the polarization of the UV light). One of these features is always considered to be determining if it represents the limiting feature for the spatial emission (e.g. beam angle). The external geometry of the UV LED chip, in particular the size of the chip's side surfaces, determines the angular radiation characteristic and can also be adjusted accordingly. Reflectors, apertures, lenses and/or shaped potting of different geometry, which can also influence emission, can be integrated into the package of a UV LED, In the case of large-area radiators, a flexible arrangement of the UV LEDs and the use of reflectors in the radiator allow the intensity to be homogenized over the irradiated area.

The spectral filter element preferably takes the form of an intrinsic Bragg reflector within the LED chip, of a Bragg reflector applied to the LED chip, or of a Bragg reflector integrated into the package. For an intrinsic Bragg reflector arranged within the LED chip, multiple $Al_xGa_{1-x}N/Al_yGa_{1-y}N$ layer pairs (x≠y) can be integrated into the epitaxial layer structure of the UV LED. A Bragg reflector applied to the LED chip may be a layer stack applied on the substrate. A Bragg reflector integrated into the package may be applied to the transparent cap (e.g. quartz cap) of an encapsulation. Alternatively, the spectral filter element may be arranged as an external optical component within the package. In the case of an arrangement of multiple UV LEDs in a common housing, the spectral filter element can be arranged analogously both on an associated transparent cover (e.g. quartz cover) and as an external optical component within the housing.

The optical element preferably comprises a lens, a light pipe, or an optical fiber. As indicated above, the optical element may be a simple exit window, e.g. in the form of the quartz cap of a package. In particular, for large-area illumination of a surface, the exit region, i.e. the region through which the emitted radiation is transmitted, may also include a lens for beam shaping or collimation. This can, for example, be integrated into a quartz cap or quartz cover, or it can also be arranged externally within the package or in a housing. A light pipe can be used to introduce the emitted radiation into body orifices that are directly accessible from the outside, such as the pharyngeal or nasal cavities. With an optical fiber as the optical element, the emitted radiation can also be applied specifically to hard-to-reach parts of the body or openings, e.g. during "minimally invasive" surgery. The preferred material for the optical elements is silica glass.

Coupling a UV LED to light pipes is intended in particular for irradiation of the nasal or pharyngeal cavity. To enable maximally efficient coupling of the light emitted by the UV LED, the light pipe should be positioned as close as possible to the UV LED. But coupling between the light pipe and the UV LED is also possible, preferably assisted by UV-transparent adhesive materials (e.g. Schott DUV 200). One or more LEDs can be used for illumination, as can also arrays of UV LEDs assembled in a common package. In the simplest case, a light pipe can be designed as a waveguide whose inner surface is reflective in the UV range (e.g. thanks to coating with aluminum). The preferred use of flexible, i.e. bendable, materials allows the light pipe to be easily brought up to the body opening or to easily reach the preferred areas to be irradiated within angled body cavities.

For filled light pipes, the filling material should be UV-transparent, preferably in the wavelength range between 210 nm and 240 nm. Suitable materials for light pipes and other UV-transparent elements include silica glass (e.g. Suprasil, Ultrasil, Infrasil), $CaF_2$, $MgF_2$ or sapphire ($Al_2O_3$). The geometry of the light pipes can be ergonomically adapted to the environments in the nasal and pharyngeal cavities. The radiation-conducting area outside the nose or mouth can be covered with a UV-reflective layer (e.g. aluminum or Teflon), which prevents UV radiation from escaping into the environment. One or more monitor diodes (photo diodes) can also be placed in this area to determine or monitor the UV radiant power and its distribution. In order to let the UV radiation escape in targeted manner at the end of the light pipe, scattering centers can be integrated locally into the light pipe. In the case of an optical waveguide made of quartz or the like, such light scatterers can be obtained, inter alia, via local roughening of the material surface.

Similarly, a fiber-coupled UV LED may be designed which is particularly suitable for application to hard-to-reach locations within the human body (e.g., ears, urethra, bladder, uterus etc.). The optical fiber may be surrounded in part by an (optionally UV-reflective) non-UV-transparent cladding, preventing UV radiation from escaping into the environment at these locations. Furthermore, the light from multiple fiber-coupled UV LEDs can be coupled together into a common optical fiber to increase the available power. In addition, .a monitor diode (photo diode) can also be integrated here as a detector in order to enable continuous determination of the UV radiant power during operation.

The optical element is preferably replaceable. This has the advantage that a device according to the invention can also be adapted to different tasks without the need for an additional radiation source. Thus, the device can be used for both large-area and spot irradiation with the same radiation source. In particular, this also allows switching between external application to a person's skin and intracorporeal application within a person's body. Another advantage is that the optical element can be cleaned and decolonized after treatment using conventional methods. In the case in particular of light pipes and optical fibers, high availability can be ensured for use of the device through rapid changeover or uncomplicated preparation. Replaceability of the optical element may also be ensured via corresponding coupling. Optical elements suitable only for single use may also be used.

A further aspect of the present invention relates to a medical pad for UV antisepsis, comprising a plurality of devices according to the invention arranged to form an array, wherein the devices are arranged on a flexible or a rigid support element. Such a pad can, for example, be applied directly to an external skin area as a kind of dressing and used for extensive UV antisepsis of the irradiated area. While the pad does not adapt to the shape of the body in the case of a rigid support element, a flexible support (e.g. made of a plastics or woven film) can also be used to adapt the shape of the pad accordingly. With a corresponding pad size, a leg or an arm, for example, can thus be enclosed virtually form-fittingly by the pad. However, a rigid support element has the advantage of allowing easy application of the pad according to the invention.

The support element preferably comprises a flexible or rigid spacer element configured to establish a distance between the devices arranged to form an array and the surface when placed on a surface to be decolonized, wherein the spacer element allows irradiation of the surface with radiation emitted by the devices. A fixed distance between the irradiated surface and the LEDs in the pad can be established by a spacer element. This means that the distance does not depend on the user and a precisely defined dose of radiation can be irradiated onto the surface. Furthermore, contamination of the LEDs can be avoided, since skin contact only occurs via the spacer element. In particular, this also allows soiling or contamination of the optical element to be avoided.

The spacer element is preferably connected replaceably to the support element. This has the advantage that the spacer element can be decolonized or sterilized using conventional methods. This allows portions of the spacer element that may be contaminated with infectious agents, i.e. in particular the points of the pad that have come into contact with the skin of a treated person, to be cleaned before further use of the pad. Several spacer elements can also be used alternately or for single use. This ensures high availability with regard to use of the pad.

At least one monitor diode is preferably integrated into the pad as a detector for monitoring the radiant power irradiated onto the surface to be decolonized. The power radiated by the pad can be monitored via the monitor diode (photo diode). By means of a large number of monitor diodes distributed over the pad, it is also possible to check whether uniform surface brightness is present.

Preferably, the UV radiation distribution can be homogenized by providing the envelope of the pad with a UV-reflecting layer on the inside (e.g. aluminum, Teflon). Outwardly, the envelope should be non-UV-transmissive to protect the environment from escaping UV radiation.

A further aspect of the invention relates to a method for in vivo antisepsis of human skin, wherein the surface of the skin is irradiated with radiation emitted by a UV LED in the UVC range, wherein the spectrum of the radiation is substantially limited to wavelengths below 235 nm, more preferably below 230 nm, and still more preferably below 225 nm, by means of a spectral filter element. The intensity maximum of the emitted radiation of the LED chip is at a wavelength below 235 nm, more preferably below 230 nm, and still more preferably below 225 nm.

The additional features and preferred further developments mentioned for the device apply mutatis mutandis to the method according to the invention. Such a method can also be used to treat chronic wounds. Chronic wounds are a favorite refuge of MRSA and have not so far been treatable with radiation therapies. This is particularly due to the fact that in the case of chronic wounds, the tissue responds very sensitively to external influences due to accompanying inflammation of the respective carrier organ (e.g. skin) and, for example, additional heat input caused by the treatment (e.g. waste heat from an excimer lamp) would represent an unacceptable burden for a person to be treated.

In a further aspect of the invention, a method for UV antisepsis is disclosed comprising irradiating a surface to be decolonized with a device according to the invention (or a pad according to the invention). The additional features and preferred further developments mentioned for the device or the pad apply mutatis mutandis to the method according to the invention.

Further preferred configurations of the invention are revealed by the remaining features mentioned in the subclaims.

The various embodiments of the invention mentioned in this application may advantageously be combined together, unless stated otherwise with regard to an individual case.

The invention is explained below with reference to exemplary embodiments and on the basis of the accompanying drawings, in which:

FIGS. 3(a)-3(c) show schematic representations of different embodiments for integrating a spectral filter element, wherein FIGS. 4(a)-(c) show schematic representations of different embodiments of devices according to the invention, where FIG. 4(b)(i) and FIG. 4(b)(ii) show an exemplary representation of a device 100 for UV antisepsis for applications in the pharyngeal cavity.

Figure 1:
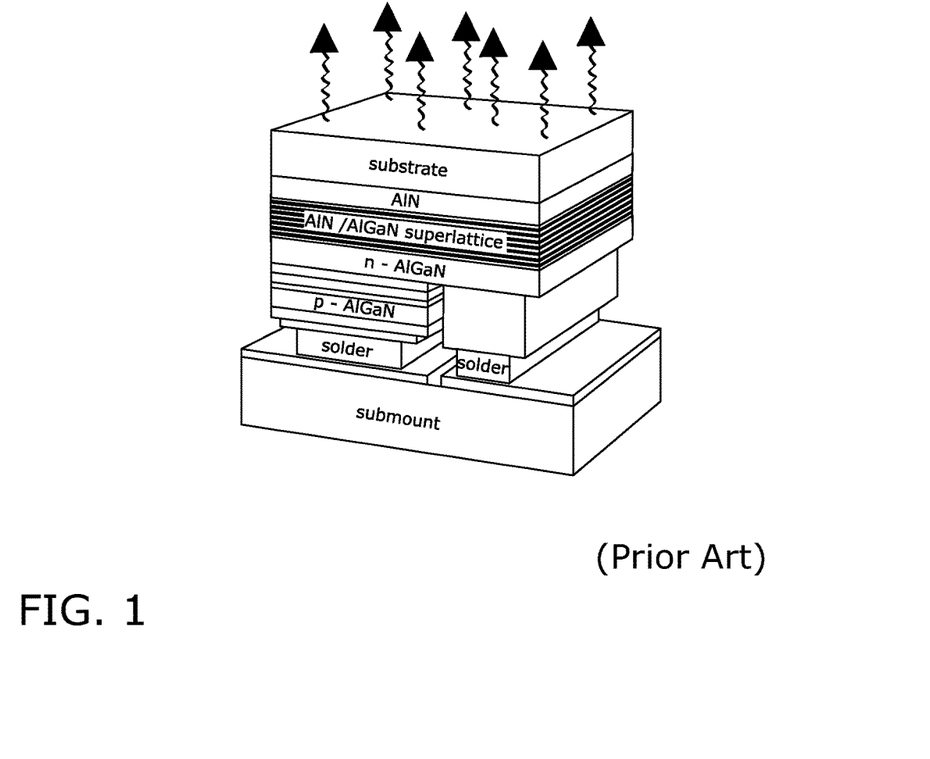
FIG. 1 shows a schematic representation of a typical layer structure of a group III nitride-based UV LED chip on a submount.

FIG. 1 is a schematic representation of a typical layer structure of a group III nitride-based UV LED chip on a submount. Usually, .either sapphire ($Al_2O_3$) or AlN is used as a substrate for producing the layer structure. Both substrate materials are in principle UV-transparent, such that the UV radiation arising in the conventional $Al_xGa_{1-x}N$ quantum films can be efficiently coupled out through the substrate. The emission wavelength of the UV LED can be adjusted by selecting the aluminum content in the $Al_xGa_{1-x}N$ quantum films and the typically surrounding $Al_yGa_{1-y}N$ quantum barriers, as well as the width of the $Al_xGa_{1-x}N$ quantum films. For emission wavelengths in the range of 210 nm to 240 nm, the aluminum contents in the quantum films range between x=0.99 and x=0.6 and the composition of the barriers ranges between y=1 and y=0.65. The width of the quantum films conventionally varies between 0.5 nm and 20 nm, wherein a quantum film thickness of about 1 nm is typically used. The number of quantum films ranges between N=1 and N=20 and is typically N=3. To allow light extraction through the substrate, any $Al_zGa_{1-z}N$ current spreading layer must also be UV-transparent. The aluminum content in the $Al_zGa_{1-z}N$ current spreading layer should therefore be selected such that this layer has a band gap greater than the photon energy of the UV radiation, i.e. the composition is preferably in the range from z=1 to z=0.65.

The width of the emission spectrum of a UV LED can likewise be influenced by the heterostructure design as well as a variation in the material composition and in the individual layer thicknesses. The adjustability of the emission wavelength of the UV LED makes it possible to optimally adapt the emission spectrum of the UV LED to the respective application. Therefore, according to the invention, for example, the best possible compromise can be established between the emitted power of the UV LED, the antiseptic effect achieved and the avoidance of damage to the irradiated tissue. As the wavelength decreases, the power and efficiency of the UV LEDs typically fall as well, i.e. the antiseptic effect becomes less or the irradiation time must be increased to achieve the same dose. However, at shorter wavelengths, UV radiation does not penetrate as deeply into the tissue surface, i.e. the damage is less. The power and efficiency of UV LEDs increase noticeably as wavelength increases, i.e. the antiseptic effect becomes stronger. However, the UV radiation penetrates deeper into tissue surfaces at longer UV wavelengths, meaning damage is greater. In addition, the typical emission spectrum of a UV LED also includes a longer-wavelength component that could potentially have a damaging effect on the irradiated tissue, in particular wavelength components in the range >240 nm that can penetrate into deeper skin layers.

Figure 2A:
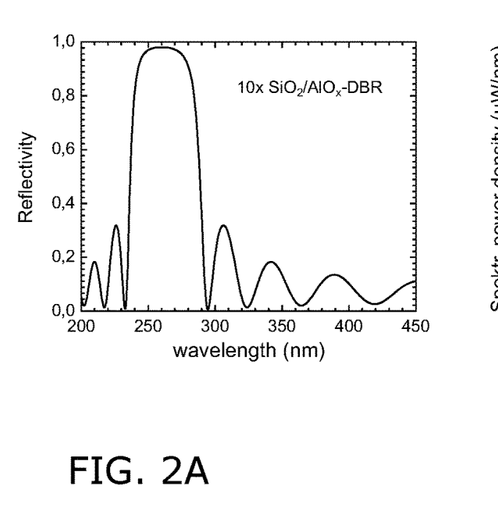
FIG. 2A shows a reflection spectrum of an $AlO_x/SiO_2$ DBR with 10 mirror layers and FIG. 2B shows the emission spectrum of a typical UV LED with such a spectral filter element (right-hand diagram)
Figure 2B:
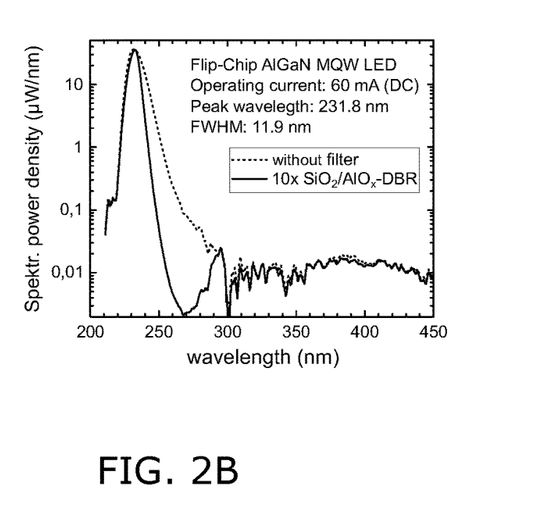

FIG. 2A shows a reflection spectrum of an $AlO_x/SiO_2$ DBR with 10 mirror and FIG. 2B shows the emission spectrum of a typical UV LED with such a spectral filter element.

The reflectance spectrum shown on the left was calculated using the transfer matrix method for perpendicular incidence. The spectral filter element consists of 10 $AlO_x/SiO_2$ mirror pairs forming a DBR (distributed Bragg reflector). For corresponding refractive indices and thicknesses for the uniform layers, the following values were assumed for $AlO_x$ n=1.85 and d=35.16 nm and for $SiO_2$ n=1.46 and d=44.52 nm. The reflectivity of the $AlO_x/SiO_2$-DBR is minimal at 233 nm (R=0.7%) and increases very rapidly for longer UV wavelengths (i.e. these wavelengths are filtered out). At a wavelength of 240 nm, reflectivity is already R=82% and at 250 nm, R=97%.

The slope of the stopband (DBR) can be adjusted by the number of mirror pairs, i.e. using more mirror pairs results in a steeper stopband. In addition, the width of the stopband (DBR) can be controlled by the choice of individual dielectrics. A higher difference in the refractive index of the dielectrics broadens the stop band (DBR).

The diagram on the right shows the emission spectrum of a typical UV LED in logarithmic representation with and without the spectral filter described above. For the UV LED without filter (dashed curve), the peak wavelength in this example is 231.8 nm and the half-value width is 11.9 nm. By integrating a filter element as described above, the longer-wavelength UV component of the emission spectrum can be significantly reduced without noticeably reducing the spectral power in the short-wavelength UV range. The peak wavelength of the UV LED with the filter (continuous curve) shifts slightly to 232.2 nm, and the half-width decreases significantly to 7.7 nm. In particular, the longer-wavelength UV component with wavelengths >240 nm is strongly reduced.

The width of the UV LED emission spectrum can also be influenced by the heterostructure design as well as a variation in the material composition and in the individual layer thicknesses.

Figure 3A:
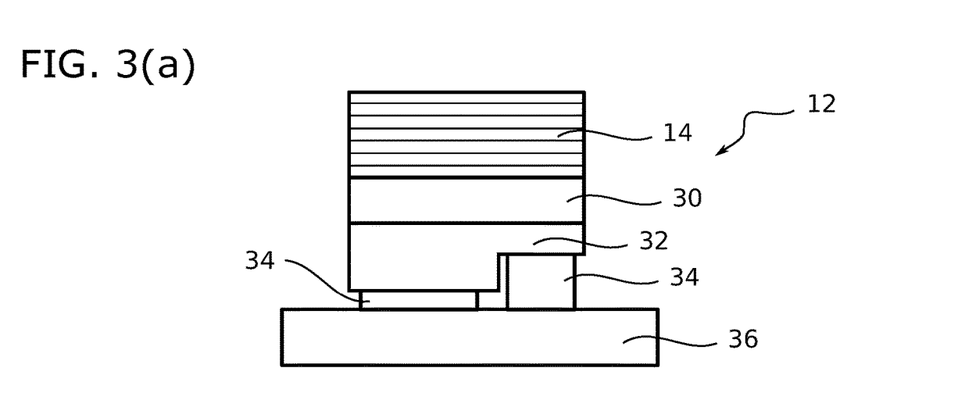
FIG. 3(a) shows a typical structure of a UV LED chip 12 on a submount 36.
Figure 3B:
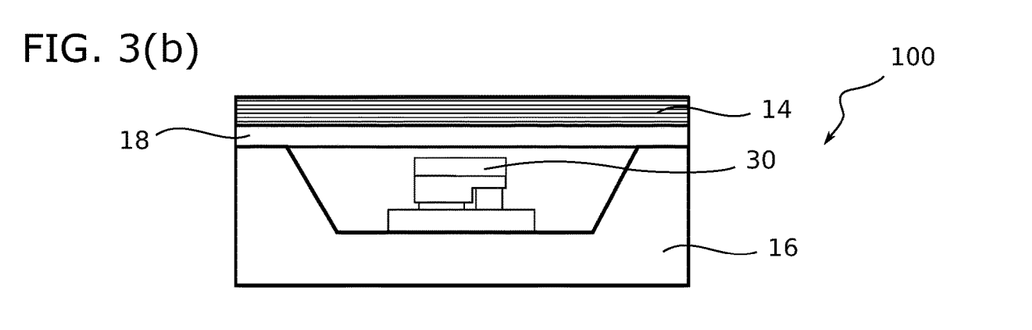
FIG. 3(b) shows the LED chip 12 described above on a submount 36 (without the spectral filter element applied) with a package 16.
Figure 3C:
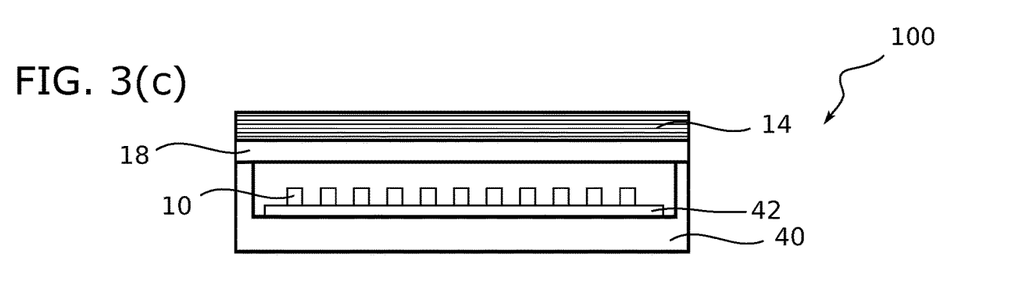
FIG. 3(c) shows multiple UV LEDs 10 (or LED chips 12) connected to form a module

FIGS. 3(a)–3(c) show schematic representations of different embodiments for integrating a spectral filter element 14.

FIG. 3(a) shows the typical structure of a UV LED chip 12 on a submount 36. The active layer 32 of the LED chip 12 is electrically conductively connected to the submount 36 via contacts 34. Connection is typically achieved using a flip-chip method, i.e. the substrate 30 of the LED chip 12 on which the corresponding semiconductor layer structure has been grown is located above the active layer 32 and is radiated through from the bottom thereof for radiation decoupling. In the embodiment shown for integrating a spectral filter element 14, the latter was applied to the free top side of the substrate 30. The spectral filter element 14 and the active layer 32 thus face each other on different sides of the substrate 30. Alternatively, the spectral filter element 14 may be arranged on the side of the active layer 32, i.e. within or adjacent to the active layer 32.

FIG. 3(b) shows the LED chip 12 described above on a submount 36 (without the spectral filter element applied) with a package 16. The package 16 protects the LED chip 12 from contamination and damage. The top of the package may have a cap that is transparent to UV radiation (e.g. exit window made of silica glass). The spectral filter element 14 may be applied to this cap. This corresponds to application to the substrate 30 according to FIG. a). In the figure shown, the cap is also intended to serve for directional emission of the emitted radiation and is thus simultaneously an optical element 18 according to the invention. The device 100 according to the invention shown could thus be used directly for local UV antisepsis.

In FIG. 3(c), multiple UV LEDs 10 (or LED chips 12) are connected to form a module. In this context, an LED 10 is understood to be an LED chip 12 with a package 16, without the need for a spectral filter element 14 or an optical element 18 according to the invention (the covering of the individual packages here merely represents an internal component and does not serve for emission purposes). The individual LEDs 10 may be arranged on a common circuit carrier 42 (e.g. PCB—printed circuit board) in a housing 40. Like the package in FIG. 3 (b), the housing 40 may have a cover that is transparent to UV radiation (e.g. exit window made of silica glass). If emission occurs directly through the cover, this is an optical element 18 according to the invention. The spectral filter element 14 can be applied to the cover.

Thus, the described module represents only a multi-LED package, the underlying principle being the same as in FIG. 3b). This embodiment is therefore merely an extended form of the package with multiple LEDs 10 or LED chips 12.

Regarding the spectral filter element, it should be noted that the FWHM half-value width of the emission spectra of UV LEDs (FWHM=full-width half-maximum) generally ranges between 5 nm and 25 nm, typically 10-12 nm. The integrated emission power between 210 nm and 235 nm is just under 300 µW and the total power over all wavelengths is about 475 µW. To avoid tissue damage from deeply penetrating UV light, the longer wavelength components (>235 nm) should as far as possible be eliminated from the spectrum. As described above, this can be done in particular by integrating a spectral filter element as an optical short-pass filter (short-pass filter with respect to wavelength) into the module or directly into the UV LED chip (e.g. onto the free substrate side) or the package. However, the spectral filter element can also be integrated into an LED module as an additional element. Such an optical short-pass filter can be obtained, for example, as a DBR (distributed Bragg reflector) using a layer stack of UV-transparent layers with different refractive indices. For this purpose, in particular, a plurality of $Al_xGa_{1-x}N/Al_yGa_{1-y}N$ layer pairs (x≠y) can be integrated into the epitaxial layer structure of the UV LEDs. Furthermore, layer pairs of dielectrics with different refractive indices can be integrated into the rear of the substrate or into the package (e.g. on a quartz cap). Other dielectrics suitable for the fabrication of DBR filters include for example $HfO_2$, $Ta_2O_5$, $CaF_2$, $MgF_2$, $Ga_2O_3$ or AlN. The spectral properties of the short-pass filter can be optimized to the respective application, in particular, by selecting suitable materials and the thickness and number of DBR mirror layers.

Figure 4A:
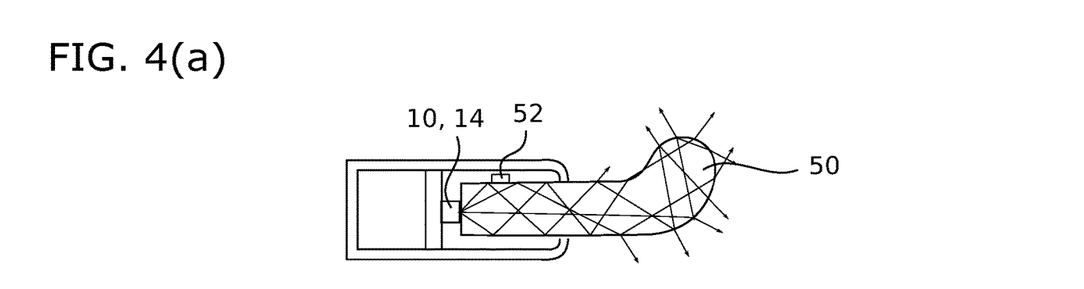
FIG. 4(a), shows an exemplary representation of a device 100 for UV antisepsis for applications in the nasal cavity.
Figure 4B:
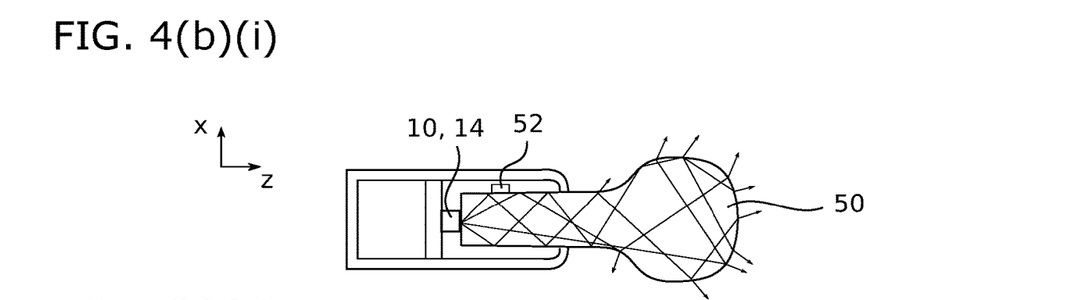
Figure 4C:
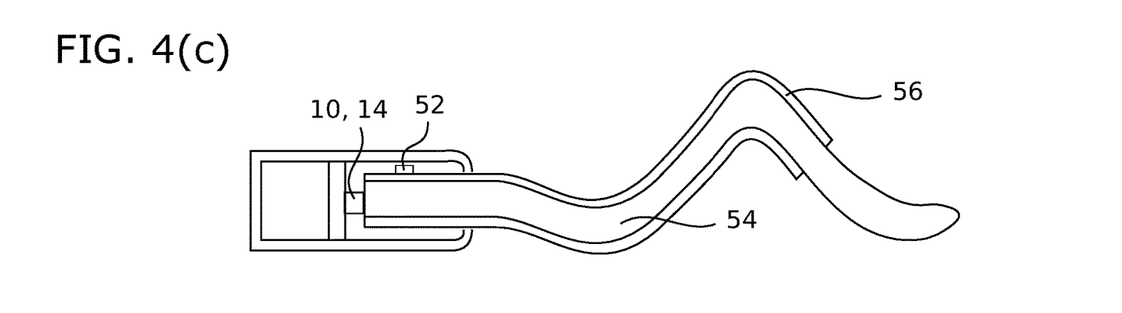
FIG. 4(c))) shows an exemplary representation of a device 100 for UV antisepsis for applications in hard-to-reach locations or narrow ducts

FIGS. 4(a)-(c) show schematic representations of various embodiments of devices 100 according to the invention. All the embodiments may optionally include one or more monitor diodes 52 for monitoring radiant power. The basic idea behind these embodiments is to adapt emission as optimally as possible to the areas to be decolonized by specific design of the optical element 18 according to the invention. In particular, body-adapted light pipes 50 and optical fibers 54 are used for this purpose. The representation should not be interpreted as limiting in terms of the use of an individual emitter. For example, instead of the combination of an LED 10 and a spectral filter element 14 shown, any of the embodiments shown in FIG. 3(a)-(c) may be used to integrate a spectral filter element 14.

FIG. 4 (a) shows an exemplary representation of a device 100 for UV antisepsis for applications in the nasal cavity. The optical element 18 according to the invention comprises a light pipe 50, which is configured to direct the radiation generated by a UV LED 10 and filtered using a spectral filter element 14 in a targeted manner into the nasal cavity of a person to be treated. In particular, the light pipe 50 can be a solid silica glass rod or a silica glass rod in the form of a waveguide. The light pipe 50 may comprise a UV-transparent filler material. The shape of the light pipe 50 is preferably adapted in size and shape to the body opening to be treated, in this case the nasal cavity. For the nasal cavity, this corresponds to a straight portion for insertion into a nostril and a spherical portion inclined relative thereto for filling the nasal cavity. In order solely to provide local irradiation of the nasal cavity, the exit area of the radiation may be restricted. In addition, it is advantageous for the light pipe 50 to be replaceable by other light pipes 50 of different sizes and shapes. This allows optimal adaptation of the irradiation to the particular user.

FIG. 4 (b)(i) and (ii) show an exemplary representation of a device 100 for UV antisepsis for applications in the pharyngeal cavity. The representation largely corresponds to that shown under FIG. 4 (a); the reference signs apply mutatis mutandis. In contrast to the representation in a), however, the shape of the light pipe 50 differs. In particular, it has a different configuration in plan view (straight portion with a directly adjacent balloon-shaped portion) FIG. 4(b)(i) and in side view (straight portion with a directly adjacent spatula-shaped portion) FIG. 4(b)(ii), corresponding to the structure of a typical human pharyngeal cavity. Here, too, it is advantageous for the size and shape of the light pipe 50 to be adaptable by exchange.

FIG. 4 (c) shows an exemplary representation of a device 100 for UV antisepsis for applications in hard-to-reach locations or narrow ducts. The representation again largely corresponds to that shown under FIG. 4(a); the reference signs apply mutatis mutandis. In contrast to the representation under a), however, the optical element 18 is not a light pipe 50, but a UV-transparent optical fiber 54 (e.g. made of silica glass). Such fibers have the advantage that they are flexible and can be bent. The fibers can thus be inserted into places that are otherwise difficult to access, such as body cavities that are not usually open to the outside. The tip of the fiber can in this case have a preferred shape for irradiation, e.g. be flat, spherical or pointed. In order to prevent UV radiation from leaving the fiber as early as the feed line, a cladding 56 that is opaque to UV radiation may be provided around a part of the fiber facing the LED 10.

Figure 5:
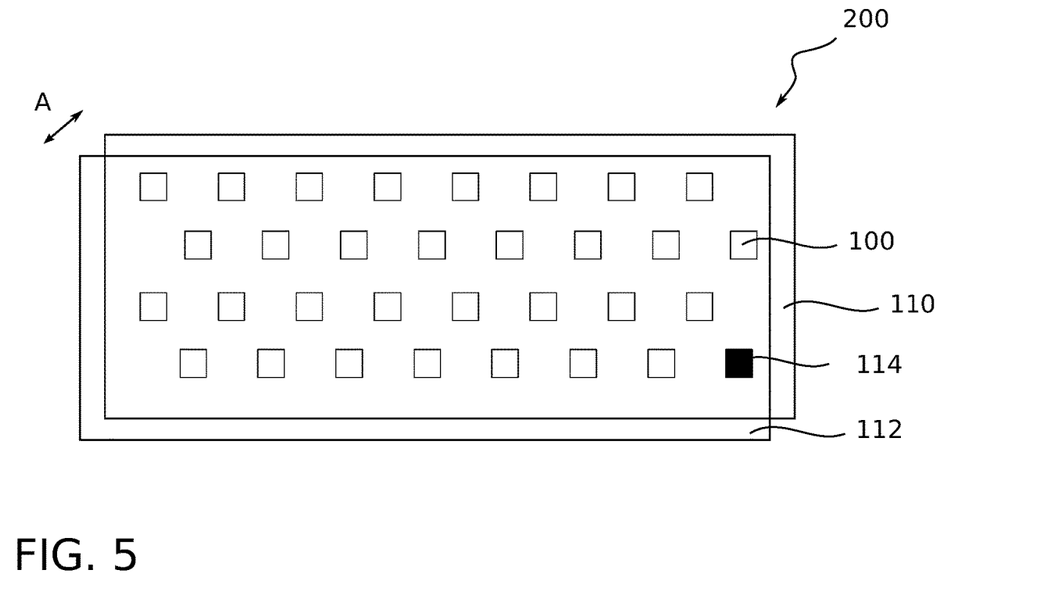
FIG. 5 shows a schematic representation of a first embodiment of a pad according to the invention.

FIG. 5 shows a schematic representation of a first embodiment of a pad 200 according to the invention, comprising a plurality of devices 100 according to the invention arranged to form an array, wherein the devices 100 are arranged on a flexible or a rigid support element 110. The support element 110 may in particular be flexible (e.g. a woven fabric). In the case of woven fabrics, the individual devices 100 may be electrically contacted using interwoven flexible feed lines. The support element 110 may comprise a flexible or rigid spacer element 112 configured to establish a distance A between the devices 100 arranged to form an array and the surface O when placed on a surface O to be decolonized, wherein the spacer element 112 allows irradiation of the surface O with radiation emitted by the devices 100. The spacer element 112 may be replaceably connected to the support element 110, in particular for reasons of hygiene. Moreover, at least one monitor diode 114 may be integrated into the pad 200 as a detector for monitoring the radiant power irradiated onto the surface O to be decolonized.

Figure 6:
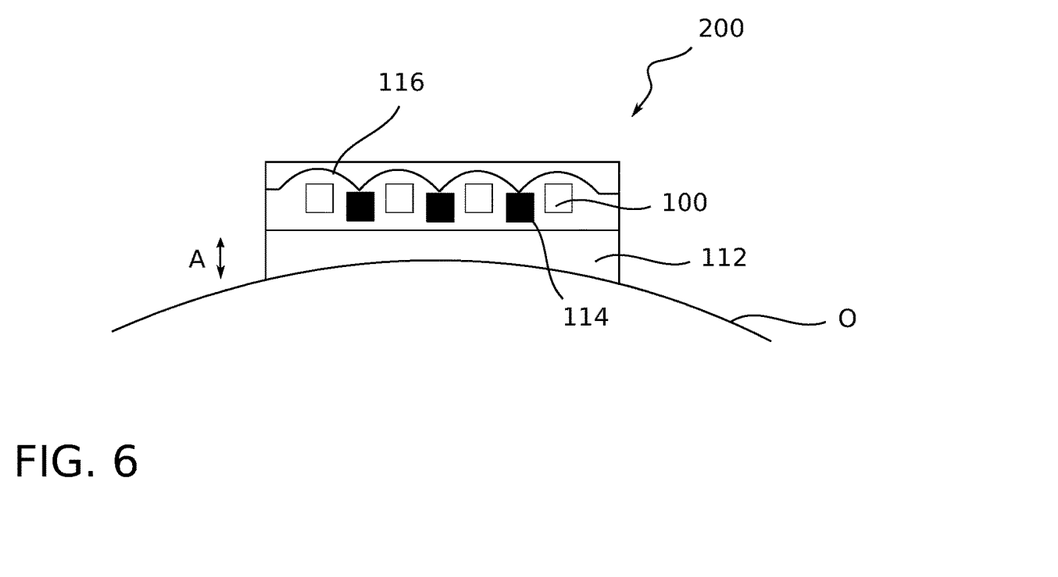
FIG. 6 shows a schematic representation of a second embodiment of a pad according to the invention.

FIG. 6 shows a schematic representation of a second embodiment of a pad 200 according to the invention. The representation largely corresponds to that shown in FIG. 5, the reference signs applying mutatis mutandis. In contrast to the representation in FIG. 5, however, a side view of a pad 200 according to the invention with a plurality of additional reflectors 116 is shown herein. In particular, this pad may be a pad with a rigid support element 110 (e.g. a (plastics) frame). The spacer element 112 is shown here by way of example with a curved bearing surface. This allows it to rest directly on a correspondingly curved surface, for example. However, both the reflectors 116 and the free configuration of the bearing surface of the spacer element 112 can also be implemented with flexible support elements 110.

Figure 7:
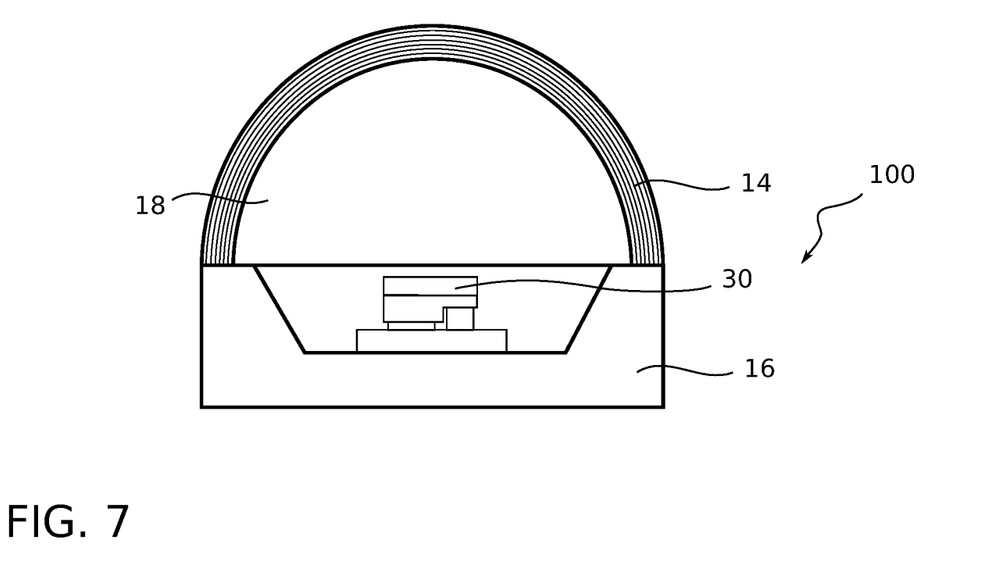
FIG. 7 shows a schematic representation of an embodiment for the integration of a spectral filter element independent of the emission angle.

FIG. 7 shows a schematic representation of an embodiment for the integration of a spectral filter element independent of the emission angle. The illustration largely corresponds to that shown in FIG. 3b); the reference signs apply mutatis mutandis. In contrast to the representation in FIG. 3b), however, the shape of the transparent cap used as optical element 18 differs. In particular, it is dome-shaped here and is located above the package 16. In the figure shown, the cap is simultaneously an optical element 18 according to the invention. However, the cap can alternatively be an internal optical element (window or lens) of a device according to the invention.

The cap can preferably take the form of a hemisphere made of e.g. UV-transparent silica glass or silicone. The individual layers of the spectral filter element 14 can be applied directly to the curved surface of the cap. This ensures that the UV light rays from the LED chip 12 are mostly perpendicular to the DBR mirror layers and that the cut-off wavelength of the spectral filter element 14 does not change with the emission angle. Another advantage is that such a configuration improves light extraction from the UV LED, so enhancing efficiency and output power. Uniform coating of the hemispherical cap can be achieved, in particular, by means of a suitable holder in a coating installation or by rotating the cap during the coating process.

If a plurality of UV LEDs 10 (or LED chips 12) corresponding to FIG. 3c) are connected together to form one module, the spectral filter element 14 may also be applied to a semi-cylindrically configured cap (or a cover) of for example UV-transparent silica glass or silicone. The representation shown in FIG. 7 would then extend into the representation plane, with the sequence of layers of the spectral filter element 14 remaining unchanged over its depth. The disadvantage of such a cylindrical arrangement is that part of the emitted UV radiation continues to impinge on the spectral filter element at an angle. However, the advantage is that LED line arrays can also be equipped with spectral filter elements 14 adapted to the emission characteristics and that a homogeneous coating of the half cylinder with dielectrics is relatively easy to implement (e.g. by rotating the half cylinder during coating).

The results of investigations into the radiation and dose dependence of UV antisepsis on excised skin samples are additionally indicated below.

The investigations were performed using a frequency-doubled argon ion laser (LEXEL laser, 95-SHG) at a wavelength of 229 nm. Excised human skin after scar removal was available for this purpose. The sample was freshly taken the day before the experiment was performed. The skin was irradiated with 0.2 mW/cm$^2$ for 5 minutes and for 30 minutes. The power was determined using a power meter. The corresponding radiation doses were 60 mJ/cm$^2$ and 300 mJ/cm$^2$. In addition, the 300 mJ/cm$^2$ was applied by 1 mW/cm$^2$ for an irradiation time of 5 min. UVB radiation at the same doses was used as a positive control. An unirradiated sample served as a negative control.

One 4 mm punch was taken from each sample and transferred to an embedding cassette. The tissue was fixed using a 4% formaldehyde solution. The samples were taken to the laboratory for analysis on the same day. Paraffin sections (thickness 1-2 μm) were prepared from the fixed tissue samples and stained with hematoxylin and eosin to allow differentiation between the different tissue structures. Typical DNA damage caused by UV radiation, known as cyclobutane-pyrimidine dimers (CPDs) and 6-4 photoproducts (6-4PP), was then detected using appropriate antibodies. CPDs constitute approximately 70% to 80% of UV-induced DNA damage, the remainder being 6-4 PPs and the isomeric forms or Dewar photoproducts thereof. DNA modification caused by both UVC and UVB irradiation should be prevented, especially in the basal membrane. Significant staining of the positive control compared to the actual samples clearly showed that radiation at 229 nm, unlike UVB radiation, produces no to few CPDs in the cells. On magnification, "CPD cells" can be found in the upper epidermis at 300 mJ/cm$^2$. The second irradiation at 300 mJ/cm$^2$ does not reveal any such cells. With UVB irradiation, on the other hand, CPD damage occurs very clearly and intensively up to the upper layers of the dermis. Furthermore, no 6-4PP damage was found with UV irradiation at 229 nm regardless of the radiation dose. In contrast, such damage is very pronounced with UVB irradiation.

It was thus possible, with these investigations, to successfully demonstrate that little to no DNA damage to excised skin samples occurs with UV irradiation at 229 nm, and even high doses of 300 mJ/cm$^2$ cause only very superficial damage to the living epidermis.

Furthermore, microbial reduction investigations were conducted on pig ears. The following antiseptic exposures were compared on marked areas of a pig's ear:
ethanol-based skin antisepsis (AHD 2000), exposure time 1 min,
UVC 60 mJ/cm$^2$, (0.2 mW/cm$^2$, 5 min),
UVC 300 mJ/cm$^2$ (0.2 mW/cm$^2$, 30 min),
UVC 300 mJ/cm$^2$ (1 mW/cm$^2$, 2.5 min) and
untreated control.

In the untreated control, only 15 colony-forming units were detectable in the sample volume of 1 ml due to the low colonization density. All the antiseptic treatment modes completely eliminated skin flora with no apparent tissue damage. This demonstrated the microbicidal effectiveness of the intended radiation range.

LIST OF REFERENCE SIGNS

10 LED
12 LED chip
14 Spectral filter element
16 Package
18 Optical element
30 Substrate
32 Active layer
34 Contacts
36 Submount
40 Housing
42 Circuit carrier
50 Light pipe
52 Monitor diode
54 Glass fiber
56 Cladding
100 Device
110 Support element
112 Spacer element
114 Monitor diode
116 Reflector
200 Pad
A Distance
O Surface

The invention claimed is:
1. A device for UV antisepsis, comprising:
a light-emitting diode chip (LED chip) configured to emit radiation in the UVC spectral range, wherein the LED chip forms a light-emitting diode (LED) with a package, wherein the LED chip has been grown on a substrate of bulk AlN or sapphire;
a spectral filter element set up substantially to limit the radiation emitted by the LED chip to wavelengths below 235 nm by means of largely angle-independent spectral filtering,
wherein the spectral filter element is integrated as an AlO$_x$/SiO$_2$-DBR or as a DBR filter with HfO$_2$, Ta$_2$O$_5$, CaF$_2$, MgF$_2$, Ga$_2$O$_3$ or AlN as dielectric into the package of the LED or is applied to the LED chip, wherein the shape of the spectral filter element is adapted to the emission characteristics of the LED such that an optical path length traversed by the radiation across the spectral filter element is essentially the same for all spatial directions; and an optical element for directional emission of the radiation emitted by the LED, wherein spatial uniformity of radiant power is achieved by adapting emission to an area to be irradiated by means of the device.

2. The device according to claim 1, wherein the spatial emission characteristics of the LED are determined by the width, composition and distortion of the band structure of the LED chip, the external geometry of the LED chip or by reflectors, apertures, lenses and/or shaped potting integrated into the package.

3. The device according to claim 1, wherein the device takes the form of a large-area radiator and intensity is homogenized over the area to be irradiated by a flexible arrangement of the LEDs and the use of reflectors in the large-area radiator.

4. The device according to claim 1, wherein the optical element comprises a lens, a light pipe or an optical fiber.

5. The device according to claim 1, wherein the optical element is replaceable.

6. A medical pad for UV antisepsis, comprising a plurality of devices according to claim 1 arranged to form an array, wherein the devices are arranged on a flexible or a rigid support element.

7. The medical pad according to claim 6, wherein the support element comprises a flexible or rigid spacer element configured to establish a distance between the devices arranged to form an array and the surface when placed on a surface to be decolonized, wherein the spacer element allows irradiation of the surface with the radiation emitted by the devices.

8. The medical pad according to claim 7, wherein the spacer element is replaceably connected to the support element.

9. The medical pad according to claim 7, wherein at least one monitor diode is integrated into the medical pad as a detector for monitoring the radiant power irradiated onto the surface to be decolonized.

10. A method for UV antisepsis comprising irradiating a surface to be decolonized using a device according to any one of claim 1.

11. The device according to claim 1, wherein the LED chip is driven for pulsed emission with pulses of a duration of up to 1 µs.

12. A device for UV antisepsis, comprising:
a light-emitting diode chip (LED chip) configured to emit radiation in the UVC spectral range, wherein the LED chip forms a light-emitting diode (LED) with a package, wherein the LED chip has been grown on a substrate of bulk AlN or sapphire;
a spectral filter element set up substantially to limit the radiation emitted by the LED chip to wavelengths below 235 nm by means of largely angle-independent spectral filtering, wherein the spectral filter element is integrated as an intrinsic Bragg reflector with a plurality of $Al_xGa_{1-x}N/Al_yGa_{1-y}N$ layer pairs with x≠y into an epitaxial layer structure of the LED chip; and
an optical element for directional emission of the radiation emitted by the LED, wherein spatial uniformity of radiant power is achieved by adapting emission to an area to be irradiated by means of the device.

13. A device for UV antisepsis, comprising:
a light-emitting diode chip (LED chip) configured to emit radiation in the UVC spectral range, wherein the LED chip forms a light-emitting diode (LED) with a package, wherein the LED chip has been grown on a substrate of bulk AlN or sapphire;
a spectral filter element set up substantially to limit the radiation emitted by the LED chip to wavelengths below 235 nm by means of largely angle-independent spectral filtering, wherein the spectral filter element is obtained as an angle-independent bandpass filter via excitation of surface plasmons or a Fabry-Pérot filter; and
an optical element for directional emission of the radiation emitted by the LED, wherein spatial uniformity of radiant power is achieved by adapting emission to an area to be irradiated by means of the device.

* * * * *